United States Patent [19]

Michalski et al.

[11] Patent Number: 5,304,372
[45] Date of Patent: Apr. 19, 1994

[54] PROCESS FOR PREPARING A HUMAN THROMBIN CONCENTRATE INTENDED FOR THERAPEUTIC USE

[75] Inventors: Catherine Michalski, Lille; Dominique Dernis, Marquette lez Lille, both of France

[73] Assignee: Association Pour l'Essor de la Transfusion Sanguine Dans la Region du Nord, Lille, France

[21] Appl. No.: 913,933

[22] Filed: Jul. 17, 1992

[30] Foreign Application Priority Data

Jul. 18, 1991 [FR] France .................. 91 09075

[51] Int. Cl.$^5$ .................. A61K 35/14; C07K 3/00; C07K 13/00
[52] U.S. Cl. .................. 424/94.64; 424/530; 530/412; 530/381
[58] Field of Search .................. 424/94.64, 530; 435/214, 188, 814; 530/386, 412

[56] References Cited

U.S. PATENT DOCUMENTS

| | | |
|---|---|---|
| 3,819,528 | 6/1974 | Berry .................. 435/188 |
| 4,447,416 | 5/1984 | Menache-Aronson et al. .................. 424/94.64 |
| 4,627,879 | 12/1986 | Rose et al. .................. 424/530 |
| 4,749,783 | 6/1988 | Gordon et al. .................. 530/412 |
| 4,965,203 | 10/1990 | Silbering et al. .................. 424/94.64 |
| 5,130,244 | 7/1992 | Nishimaki et al. .................. 424/94.64 |
| 5,143,838 | 9/1992 | Kraus et al. .................. 435/214 |
| 5,149,540 | 9/1992 | Kunihiro et al. .................. 424/94.64 |
| 5,151,355 | 9/1992 | Crowley et al. .................. 424/94.64 |
| 5,151,499 | 9/1992 | Kameyama et al. .................. 530/386 |

FOREIGN PATENT DOCUMENTS

| | | |
|---|---|---|
| 378798A1 | 12/1989 | European Pat. Off. . |
| 0443724 | 8/1991 | European Pat. Off. . |
| 0505604 | 9/1992 | European Pat. Off. . |

OTHER PUBLICATIONS

"Human Thrombins Production, Evaluation, and Properties of -Thrombin*" Journal Biological Chemistry, vol. 262, No. 11, Jun. 10, pp. 3587-3598, 1977.

"Note on the Preparation of Bovine Thrombin" Thrombosis Research 20; pp. 281-283 1980.

"Purification de la Thrombine Humaine Par Chromatographie d'Affinite en vue de son Utilisation Dans les Preparations de Colle Biologique" Manuscript recu le 6.07.89. Accepte le 3.10.89.

"The Purification and Properties of Bovine Thrombin" The Journal of Biological Chemistry, vol. 245, No. 19, Oct. 10, pp. 4857-4862, 1970.

"A Rapid Method For The Purification of Bovine Thrombin & The Inhibition of the Purified Enzyme W/Phenylmethylsulfonyl Fluoride*" Biochemistry vol. 10, No. 13, 1971.

"Purification of Thrombin by Affinity Chromatography on Immobilized Heparin" vol. 11, pp. 799-808, 1977.

(List continued on next page.)

Primary Examiner—Douglas W. Robinson
Assistant Examiner—Kristin Larson
Attorney, Agent, or Firm—Birch, Stewart, Kolasch & Birch

[57] ABSTRACT

Process for preparing a human thrombin concentrate from the PPSB fraction of plasma that does not involve any addition of factors of animal origin to induce activation of the prothrombin to produce thrombin, and which includes a viral inactivation step using solvent-detergent and purification by cation exchange chromatography. The choice of a protective medium ensures the high specific activity of the final product. The thrombin concentrate obtained using this process is intended for therapeutic use, either alone, to serve as a local hemostatic agent, or in combination with a fibrinogen concentrate to form biological glue.

8 Claims, No Drawings

OTHER PUBLICATIONS

"Affinity Chromatography: Purification of Bovine Trypsin and Thrombin[1]" Biochemistry & Biophysics 154, 501–599 (1973).

"Thrombin Purification by One-Step Preparative Affinity Chromatography on Modified Polystyrenes" Journal of Chromatography, 363 (1986) 95–100.

"Large-Scale Preparation and Preliminary Characterization of Human Thrombin" BioChem. Biophys. Acta, 229 (1971) 26–32.

"Reactifs Biochimiques et Organiques" 1990 Lisle d'abreau Chesnes BP. 701, 38297 La Verpilliere Cedex, France PCT/US83/000549 filed on Apr. 14, 1983.

"Purification De La Prothrombine Humaine Par Chromatographie Sur Deae-Sephadex Properties De La Prothrombine Purifiee" 1968, vol. 1.

"Bovine Thrombin and Activated Faxtor X" The Journal of biological Chemistry, vol. 243, No. Jan. 10, pp. 112–117, 1968.

"Bovine Thrombin Purification and Certain Properties" The Journal of Biological Chemistry, vol. 242, No. 22, Nov. 25, pp. 5252–5250, 1967.

"Multiple Bovine Thrombin Components*" The Journal of Biological Chemistry, vol. 245, No. 19, Oct. 10, pp. 5049–5056, 1970.

PROCESS FOR PREPARING A HUMAN THROMBIN CONCENTRATE INTENDED FOR THERAPEUTIC USE

BACKGROUND OF THE INVENTION

1. Field of the Invention

The present invention relates to a process for preparing a human thrombin concentrate intended for therapeutic use, purified on an industrial scale from an isolated fraction of human plasma.

Thrombin is a serine-protease generated in the blood stream through activation of its inactive precursor, prothrombin. It plays a fundamental part in the coagulation process: it cuts the fibrinogen into fibrin monomers and, through proteolytic cutting, it activates Factor XIII which stabilizes the fibrin network.

It also plays a part in other physiological processes: it initiates the secretion and platelet aggregation reactions, thus facilitating the formation of the white plug. It also activates the proteins of the complement system. It has a mitogenic effect on the fibroblasts, which accelerates the healing of the damaged blood vessels.

As a result of these different properties, thrombin has therapeutic applications as a local haemostatic agent. At the present time, animal thrombin, equine or bovine, is used clinically in said therapeutic applications. These preparations are not always perfectly purified and their application can be the cause of immunological reactions due to the overload of heterologous proteins. The use of bovine thrombin further carries the risk of transmitting infectious diseases recently diagnosed and as et controlled with difficulty, such as spongiform bovine encephalitis (or "mad cow disease").

Thrombin purification, like that of many enzymes, poses problems as regards maintaining its total enzymatic activity. Native $\alpha$-thrombin is, in fact, generally unstable and, through autolysis or limited proteolysis, it yields derivatives, $\beta$- and $\gamma$- thrombins that have lost a substantial part of their coagulating activity on fibrinogen.

Thrombin purification processes also have the drawback of being unpredictable with regard to scale-up from the laboratory or bench scale to an industrial scale. Given the large amounts of blood involved in industrial scale processes, this drawback is significant.

2. Description of Related Art

Known purification techniques apply especially to bovine thrombin: the include chromatography on ion exchange resins such as DEAE-cellulose (Yin et al. J. Biol. Chem., 1968, 243 112); possibly associated with filtration on SEPHADEX G 100 ® (Baughman et al. J. Biol. Chem., 1967, 242, 5252-5259); certain methods can be used to separate the $\beta$ and $\gamma$ forms on a phosphocellulose column (Rosenberg et al., J. Biol.Chem. 1970,245,5049)and through the association of several types of ion exchange chromatography (Batt et al. J. Biol. Chem. 1970, 245, 4857).

New resins have also been used, such as sulphoethyl or sulphopropyl SEPHADEX (Lundblad-Biochemistry, 1971, 10, 2501) as well as affinity chromatographies on supports such as heparin-SEPHAROSE (Nordeman et al. Thromb. Res., 1977, 11, 799–888) and p-aminobenzamidine-agarose (Hixson et al. Arch. Biochem. Biophys., 1973, 154,501).

Two publications describe the purification of human thrombin, one on benzamidine-SPHERODEX (Lorne et al. Rev. Fr. Transf. Hémobiol., 1989, 32, 391–403), but the product only exhibits low activity (11 to 20 NIH U/ml), and the other on new polystyrenes (Fischer et al. J. Chromatography, 1986, 363, 95–100), but this Product contains bovine Factor V (see below).

To obtain thrombin, it is necessary to have at one's disposal not only a source of its precursor, prothrombin, but also, depending on the mode of activation chosen, a sufficient concentration of the other coagulation factors involved in the activation process. Various methods have been described permitting the activation of prothrombin to produce thrombin. Fenton et al. (Biochim Biophys. Acta, 1971, 229, 26-32 and J. Biol. Chem., 1977, 252, 3587-3598) describe the preparation of thrombin from Cohn's fraction III extracted on resin, through the addition of calcium chloride and tissue thromboplastin extracted from the human brain. The reaction can be accelerated by the addition of Factor V of bovine origin (Bernamon-Djiane-Coagulation, 1968, 1, 259).

Specific activators extracted from snake venoms can also be used (Gosh et al. Thromb. Res., 1980, 20, 281).

However, these different methods present major drawbacks when one contemplates preparing very large volumes of human thrombin intended for therapeutic use. For instance, thromboplastin from the human brain is difficult to obtain and represents a limiting factor when it comes to treating several hundred liters of plasma. It is difficult to make activation with viper venom compatible with use in man, unless there is a high-performance system available to enable it to be eliminated subsequently. The use of bovine Factor V has proven particularly dangerous because the residual quantities that may be injected into patients are the origin of serious immunological reactions.

SUMMARY OF THE INVENTION

To avoid these problems, Applicants have developed a process permitting the preparation of purified, concentrated human thrombin that does not include any addition of heterologous material and which, in addition, has undergone a viral inactivation treatment. The process is simple and compatible with an application to large volumes, on an industrial scale.

The original material is the PPSB fraction of human Plasma (PPSB: proconvertin or F VII, prothrombin, Stuart factor or Factor X and antihaemophilic factor B or Factor IX); thus, all the molecules needed to activate the prothrombin are present in the initial mixture: Factors VII, IX, X, phospholipids and cofactors V and VIII.

The process implemented by the Applicant comprises the following 6 consecutive steps:

a) The cryoprecipitated plasma supernatant is adsorbed on DEAE-SEPHADEX ®, dextran 2-(diethylamino)ethyl 2-[[2-(diethylamino)ethyl]-diethylammonio]ethyl ether chloride hydrochloride epichlorohydrin crosslinked, and washed in citrate buffer solution at a pH of 7 containing 0.20M to 0.23M, and preferably 0.23M, of sodium chloride, which makes it possible to eliminate the fibrinogen and the traces of inhibitors that would slow down the following thrombin activation reaction. The PPSB is then eluted by increasing the sodium chloride concentration to 0.50M.

b) Activation of the prothrombin to produce thrombin is initiated by the addition of calcium chloride at a final concentration of between 6 and 10 mM, and preferably 7 mM. (It has been observed that an excess of CaCl$_2$ inhibited the activation reaction). This step includes a first incubation period of short duration, followed by a second, longer period at a lower temperature.

The mixture is thus incubated, initially, at 37° C. for 2 hours. This treatment alone enables 300 to 350 NIH U of thrombin per ml of PPSB (NIH U: units defined by the National Institute of Health - USA) to be generated. Longer incubation at this temperature was not found to improve the result.

Incubation is then continued at 24° C. for at least 16 hours, which made it possible to obtain from 700 to 1000 NIH U of thrombin/ml of PPSB.

c) The PPSB thus recalcified is subjected, as it is, to a viral inactivation treatment using solvent-detergent and, more particularly, by adding 0.3% TnBp/1% Tween; incubation is continued at 24° C. for at least 6 hours and, generally speaking, overnight. It should be noted that it is important to carry out this treatment after the thrombin has been activated because, if it is carried out before, that is to say directly on the PPSB, factors such as the phospholipids, which are necessary for the activation reaction, would be eliminated.

d) The thrombin is then purified by means of a single step of ion exchange chromatography, and more particularly on a strong cation exchanger. Preferably, use is made of a rigid gel formed by an agarose matrix grafted with CH$_2$—SO$_3$ groups, for example S-SEPHAROSE FF ®, a rigid gel, formed by an agarose matrix grafted with CH$_2$—SO$_3$ groups (Pharmacia). Chromatography was carried out in a medium including 40 mM of sodium gluconate and 0.01M of sodium chloride, at a pH of 6.5. Sodium gluconate has a highly beneficial protective effect on the biological activity of thrombin.

After the thrombin has been adsorbed on the column, the latter is washed in a medium comprising 150 mM of sodium gluconate and 0.04M of NaCl at a pH of 6.5.

The thrombin elution conditions are adjusted to obtain a narrow chromatographic peak, and, more particularly, by increasing the sodium chloride concentration to 0.2M and the sodium gluconate concentration to 150 mM.

The use of a sodium gluconate base medium further has the advantage of avoiding the dialysis step, which is essential with the use of the conventional phosphate buffer solutions.

e) Once it has been eluted from the chromatography column, a mixture of stabilizers including 2 g/l of albumin, 5 g/l of saccharose and 60 mM of CaCl$_2$ is added to the thrombin in solution in the gluconate buffer, the role of these stabilizers being particularly important in the following step.

f) The thrombin preparation is then concentrated, preferably by ultrafiltration, aliquoted in volumes adapted to the purposes of subsequent therapeutic use, and freeze-dried.

The presence of albumin as a stabilizer proved essential during the concentration step.

It was found that saccharose, in preference to all other sugars and amino acids that were tested, had a very important stabilizing effect on the concentrate in a liquid state, during the dispensing step, which can take a very long time when the solution is aliquoted in volumes of 1 to 5 ml.

The presence of CaCl$_2$ and of saccharose proved vital for stabilizing purposes during freeze-drying.

The process according to the present invention presents several features that clearly distinguish it from the other processes described (more particularly Lorne et al. and Fischer et al., mentioned above) and which endow the final product with its remarkable advantages of purity and very high specific activity.

To summarize, these features are as follows:
 the use of a pre-washed PPSB fraction from which the fibrinogen and inhibitors have been removed;
 the choice of recalcification conditions: calcium chloride concentration and 2 successive incubation temperatures:
 viral inactivation treatment using solvent-detergent carried out between the thrombin activation and purification steps and not on the PPSB, as would appear desirable for reasons of manipulation safety, but which, at this stage, denatures the phospholipids that are necessary for the thrombin activation reaction;
 chromatography on a strong cation exchanger gel and the use, in this step, of a specific protective medium containing sodium gluconate;
 the choice of a mixture of stabilizers for the final product that protects its activity during the last 3 manipulations: concentration, dispensing and freeze-drying.

The object of the invention is consequently to provide a process for preparing a human thrombin concentrate for therapeutic use comprising purification by chromatography of a PPSB fraction of plasma previously recalcified by the addition of CaCl$_2$ including, more particularly, treatment of the initial PPSB fraction to remove the fibrinogen and the thrombin activation inhibitors, by washing with sodium chloride, followed by purification by chromatography on a strong cation exchanger gel, in the presence of sodium gluconate.

According to another feature of the invention, the process includes a viral inactivation treatment using solvent-detergent which is carried out after recalcification of the washed PPSB fraction and before purification of the activated thrombin by chromatography.

According to another feature of the invention, the process includes the addition, to the solution of thrombin eluted from the chromatography column, of a mixture of stabilizers including albumin, saccharose and calcium chloride.

DETAILED DESCRIPTION OF THE INVENTION

A remarkable feature of the process is its efficiency with very large amounts of starting material thus allowing the production, in a single batch, of up to 16 million NIH U of thrombin (which represents 150 times more than with another known process, as described in EPA 0 378 798) and without interfering with the purification of other blood-derived products of major economic importance (such as blood coagulation factors, albumin, immunoglobulins...).

The object of the present invention extends to the thrombin concentrate obtained using the process described and which is characterized by a coagulating activity at least equal to 500 NIH U/ml and a specific activity at least equal to 1000 NIH U/mg of proteins.

Its high concentration and its specific activity distinguish the concentrate according to the invention from another product prepared according to another process (Lorne et al., mentioned earlier) and which only attains an activity of 11 to 20 NIH U/ml.

Moreover this freeze-dried concentrate is remarkably stable, its coagulating activity remaining constant for at least one year.

The thrombin concentrate according to the present invention is thus perfectly adapted to therapeutic use in man.

It can be used, as it is, as a local haemostatic agent.

It can also be used to form biological glue by addition to a fibrinogen concentrate including small quantities of Factor XIII and of fibronectin, as described by the Applicant in patent application EP-0 305 243. The biological glue forming process reproduces the last stage in coagulation, that is to say the formation of the fibrin network. Thrombin cuts the fibrinogen molecule into fibrin monomers. It activates factor XIII in the presence of calcium ions, which factor, in its activated form, stabilizes the soluble fibrin in an insoluble clot, which is firm and non-friable. The haemostatic power of the product thus makes it possible to limit bleeding during and after operations and to reinforce local haemostasis in patients with a constitutional or acquired coagulation deficiency (particularly patients under treated with an anticoagulant).

The following examples illustrate the invention without limiting the scope thereof.

EXAMPLE 1 a—Preparation of the PPSB fraction

The original material was a plasma cryoprecipitate supernatant that was obtained by thawing and centrifuging at 0° to 3° C.

1000 to 1500 liters of supernatant were adsorbed on DEAE-SEPHADEX A50 ® in the presence of physiological serum, in a proportion of 1.5 g of resin per liters of supernatant. After washing with 0.23M of sodium chloride in an 0.01M citrate buffer solution at a pH of 7, the PPSB was eluted with 0.50M of sodium chloride in the same buffer solution and concentrated to 40 g/l of proteins, and 2.5 g/l of lysine were added thereto. It was then adjusted to an osmolarity of approximately 290 mOsm/l at a pH of 7.0.

The PPSB thus prepared contained, in addition to the prothrombin at a concentration of approximately 50 U/ml, coagulation factors X, IX and VII at respective concentrations of approximately 45 U/ml, 45 U/ml and 5 U/ml. It also contained 5 to 6 U/ml of factors Vc and VIIIc, as well as phospholipids the presence of which was revealed by the thrombin generation time (or TGT 50).

Washing with sodium chloride made it possible to remove the fibrinogen, as well as certain inhibitors which, when they are present in the PPSB, slow down the recalcification reaction.

b—Recalcification conditions 9 to 11 liters of PPSB, freshly prepared or after thawing, were filtered under sterile conditions, 7 ml of CaCl$_2$ per liter of PPSB then being added thereto, in a beaker or in a sterile 30-liter stainless steel tank, and placed in a water bath at 37° C., for 2 hours. After this first step, approximately 300 NIH U of thrombin/ml were obtained.

The temperature was then lowered to 24° C. and the mixture was kept at this temperature for a further 16 hours. The thrombin yield obtained at the end of treatment was 700 to 1000 NIH units/ml of PPSB.

The specific activity of the thrombin at this stage, represented 20 to 40 NIH U/mg of proteins.

c—Viral inactivation

Inactivation of any viral contaminants was effected by adding 0.3% TnBP and 1% Tween 80 (final concentrations), at a temperature of 24° C., for at least 6 hours. In practice, the mixture was left overnight in the TnBP/Tween 80 medium.

No loss of thrombin activity was observed during this step. The specific activity of the thrombin at the end of TnBP/Tween 80 treatment represented 20 to 40 NIH U/mg of proteins.

The mixture was then dee frozen at −30° C., in plastic bags in samples of 1 to 3 liters.

d—Thrombin purification

The purpose of this step was to separate the thrombin from the reaction mixture containing the TnBP/Tween 80, the activated coagulation factors and any other proteins of the PPSB that could be partially degraded by the serine-proteases.

Chromatography was carried out on a strong cation exchanger gel S-SEPHAROSE FF ® (Pharmacia), which is a rigid gel, formed by an agarose matrix grafted with CH$_2$—SO$_3$ groups.

The thrombin, which is unstable, was protected during chromatography by the use of sodium gluconate at a pH of 6.5, under the following conditions: after thawing, 10 to 12 liters of PPSB/thrombin/solvent-detergent residues were adjusted to a pH of 6.5 and then injected onto a column of approximately 16 liter of S-SEPHAROSE FF ® equilibrated with a medium containing 40 mM of sodium gluconate and 0.01M of NaCl, at a pH of 6.5. The majority of the proteins of the PPSB, as well as the TnBP and the Tween 80, were not retained by the column. The gel was then subjected to washing with a 150 mM sodium gluconate, 0.04M NaCl medium, at a pH of 6.5. The thrombin was then eluted by adding 0.20M of sodium chloride to the same medium.

Once it had been eluted from the column, the thrombin was harvested in the presence of the following stabilizers: 2 g/l of albumin, 5 g/l of saccharose and 60 mM calcium chloride. The product was then concentrated by ultrafiltration, adjusted to an albumin concentration of 5 g/l and to a pH of 6.3-6.5.

The overall yield of these 2 steps, chromatography and concentration, was in the order of 90%.

After sterilizing filtration, the product was dispensed in volumes of 5 ml, 2 ml, 1 ml or 0.5 ml, depending on its intended subsequent use in the form of biological glues, and freeze-dried. The presence of the stabilizers was required in order to maintain the enzymatic activity of the thrombin during these treatments, as shown in Tables I and II.

TABLE I

| | Stability of eluate during dispensing THROMBIN NIH U/ml | | | |
|---|---|---|---|---|
| | To | To + 3 hrs., 30 min. | To + 5 hrs., 30 min. | Residual activity |
| Eluate untreated | 429 | 371 | 391 | 91% |
| 60 mM CaCl$_2$ saccharose 5 g/l | 425 | 384 | 374 | 88% |
| 60 mM CaCl$_2$ saccharose 5 g/l albumin 5 g/l | — | 384 | 380 | 98% |

TABLE II

| Stability of preparation in liquid form | | | |
|---|---|---|---|
| | Thrombin in NIH U/ml | | Residual |
| | To | To+ 2 weeks | activity |
| CaCl₂ saccharose albumin | 549 | 535 | 97% |
| CaCl₂ saccharose glycine | 557 | 389 | 70% |
| CaC₂ albumin glycine | 621 | 518 | 83% |
| CaCl₂ only | 534 | 503 | 94% |

EXAMPLE 2

Characteristics of the product

The thrombin concentrate was in freeze-dried form. After reconstitution in distilled water, it was evaluated according to the following methods:

a—Coagulating activity

The activity of the native alpha-thrombin was measured by its fibrinogen coagulating activity. It was expressed in NIH (National Institute of Health) units in relation to a standard reference: NIH thrombin, batch J.

After reconstitution in distilled water, 6 dilutions of 1/300 to 1/900 were prepared in Owen Koller buffer solution (L'Hémostase: méthode d'éxploration et diagnostic pratique. Ed. L'Expansion scientifique K. J. CAEN - H. J. LARRIEU. M. SAMAMA.) containing 0.5% polyethylene-lycol 6000. The coagulation time was measured using a KC 10 Amelung apparatus (BAXTER). 200 μl of dilution (standard or sample to be tested) were placed in a series of cups. After 1 minute at 37° C., 200 μl of 1 g/l fibrinogen were added, and the stop watch was started. The standard curve was plotted on bilogarithmic paper. The times obtained for the samples to be tested were noted and their NIH U/ml rate was deduced on the graph.

b—Amidolytic activity

The amidolytic activity of the thrombin was determined on the STAGO chromothrombin substrate in accordance with the supplier's instructions. It was expressed in nkat/ml. The relation between the nanokatals and the NIH units was 1 NIH U=2 nkat.

The activity found on the chromogenic substrate corresponded to the activity of the native alpha-thrombin as well as to that of its proteolysis derivatives: β and γ thrombins.

c—Protein concentration

The protein concentration was determined using the Biuret method.

d—Electrophoresis on polyacrylamide gel

Electrophoresis was carried out on the Pharmacia PHAST SYSTEM® with Phast gel 10/15 in SDS medium.

e—properties of the biological glue formed by coagulation of the concentrate of fibrinogen, Factor XIII and fibronectin in the presence of thrombin (European patent 0 305 243).

The properties of the biological glue formed in the presence of thrombin were evaluated using the following parameters: clotting rate (in seconds) and adhesive power on mouse (g/cm²). The displacement time 50 (in seconds) and the total displacement (in radians) were measured using a rheometer.

Characteristics of the thrombin concentrate

The characteristics measured using the methods described above are set forth in the following table.

TABLE III

| Characteristics of the human thrombin concentrates | | | | |
|---|---|---|---|---|
| Batch No. | 06510010 | 06510020 | 06510031 | 06510032 |
| Reconstitution volume (ml) | 5.2 | 2.2 | 1.2 | 5.2 |
| Coagulating thrombin in NIH U/ml | 610 | 540 | 564 | 522 |
| Amidolytic thrombin in NIH U/ml | 688 | 587 | 764 | 739 |
| Protein concentration | | | | |
| g/l | 8 | 7 | 7 | 6.5 |
| pH | 6.25 | 6.27 | 6.30 | 6.41 |
| Calcium concentration in mmoles/l | 55 | 56 | 60 | 75 |
| Osmolarity in mOsm/l | 594 | 539 | 554 | 570 |
| Sacccharose in g/l | 2.25 | 4.8 | 5.1 | 4.3 |
| Albumin in g/l | 6.6 | 6.4 | 6.2 | 6.0 |
| gelification time (in seconds) | 6 | 6 | 5 | 7 |
| half-displacement time (in seconds) | 0.77 | 0.57 | 0.81 | 0.58 |
| Total displacement (in radians) | 0.60 | 0.36 | 0.60 | 0.34 |
| Adhesive strength in g/cm₂ | 130 | 160 | 137 | 142 |

Coagulating activity in the concentrates was in the order of 550 NIH U/ml.

Amidolytic activity was of the same order, 600–700 NIH U/ml, demonstrating the absence of a high proportion of degraded forms, β and γ-thrombins.

The purity of the product was evaluated by electrophoresis on polyacrylamide gel. In an SDS medium, one observed, in addition to the band corresponding to the albumin with a molecular weight of 67,000 daltons, a single major band corresponding to α-thrombin with a molecular weight of 36,000 daltons. After reduction by β-mercapto-ethanol, there appeared a band corresponding to the heavy chain of the α-thrombin, with a lower molecular weight. The light chain of approximately 4,000 daltons had migrated off the plate.

The stability of the product after reconstitution was tested (Table IV). The thrombin was stable for at least 24 hours in liquid state. It was also stable in deep-frozen form (Table V), as well as in freeze-dried form (Table VI). This stability was ensured by the gluconate-saccharose-calcium chloride-albumin medium with a pH of 6.5.

TABLE IV

| Stability of the thrombin after reconstitution | | |
|---|---|---|
| | Coagulating activity (in NIH U/ml) | |
| (batch No.) | 06510010 5 ml | 06510020 2 ml |
| To | 569 | 595 |
| To + 3 H | 590 | 614 |
| To + 6 H | 596 | 619 |
| To + 24 H | 539 | 545 |

TABLE V

| Stability of thrombin in deep-frozen form | | |
|---|---|---|
| | Coagulating activity (in NIH U/ml) | |
| (batch No.) | 06510020 | 06510031 | 06510032 |
| To | 610 | 598 | 595 |

TABLE V-continued

Stability of thrombin in deep-frozen form

| (batch No.) | Coagulating activity (in NIH U/ml) | | |
|---|---|---|---|
| | 06510020 | 06510031 | 06510032 |
| To + 1 month | 611 | 628 | 582 |

TABLE VI

Stability of thrombin in freeze-dried form at +4° C.

| Batch 06510010 | Coagulating activity (NIH U/ml) | gelification time (s) | half-displacement time 50 (s) | Total displ. (rad) | Adhesive strength (g/cm$^2$) |
|---|---|---|---|---|---|
| To | 610 | 6 | 0.77 | 0.60 | 130 |
| To + 1 month | 619 | 6 | 0.63 | 0.44 | / |
| To + 2 months | 609 | 7 | 0.62 | 0.39 | 155 |
| To + 3 months | 573 | 5 | 0.56 | 0.29 | 135 |
| To + 12 months | 584 | 5 | 0.56 | 0.30 | 143 |

The stability of the freeze-dried thrombin was also measured in an "accelerated ageing" test (Table VII).

TABLE VII

Stability of thrombin in freeze-dried form (5 ml) at 45° C.

| Batch 06510010 | Coagulating activity (NIH U/ml) | gelification time (s) | half-displacement time 50 (s) | Total displ. (rad) | Adhesive strength (g/cm$^2$) |
|---|---|---|---|---|---|
| To | 610 | 6 | 0.77 | 0.60 | 130 |
| To + 3 weeks | 508 | 6 | 0.65 | 0.43 | 151 |
| To + 6 weeks | 520 | 8 | 0.83 | 0.70 | 152 |
| To + 10 weeks | 580 | 3 | 0.45 | 0.20 | 180 |
| To + 3 months | 555 | 5 | 0.71 | 0.44 | — |

The rheological properties of the biological glue obtained in the presence of human thrombin or bovine thrombin were compared using the conventional test procedures.

The study was performed with the same fibrinogen concentrate, which was mixed with a bovine or human thrombin (06510010). The procedures used for each test were rigorously identical. The equipment was a CARRIMED CSL 100 controlled-stress rheometer.

a—Use in creep mode

Measurement of gelification time

The half displacement times t1 and t2 (time required to obtain 50% of total displacement), were:
t2 (bovine thrombin): 1.8 s.
t1 (human thrombin): 0.77 s.
No significant difference.

Elasticity study

The two products were found to have identical instantaneous elasticity.

b—Use in oscillation mode.

A breaking point of approximately 2500 N/m$^2$ was found for the two products.

The storage modules G' of the two glues progressed similarly in time.

The storage module G' as a function of frequency was comparable for the two products.

All the results confirmed the observations made on using the product, as regards the aspect of the clot, the exsudation and the gelification time.

All of the results allowed to conclude that the rheological characteristics and the mechanical properties of the glue obtained in the presence of the human thrombin were identical with those obtained in the presence of the bovine thrombin, which is presently the constituent of biological glues in common use.

EXAMPLE 3

Scaling up of the process

The process as described in example 1 was used with several batches of 10–15 liters of PPSB with the same efficiency as shown on table VIII.

The yield of the further chromatography-concentration step is between 89 and 100%.

The process as a whole thus allows the production of well standardized batches containing more than 10 million NIH units of thrombin.

TABLE VIII

Coagulating activity of thrombin after recalcification step and viral inactivation

| Batch n° | starting volume (ml) of PPSB | Total amount of thrombin produced (NIH U) per batch |
|---|---|---|
| 96510040 | 10 000 | 9 276 660 |
| 96510050 | 10 570 | 9 163 440 |
| 96510060 | 16 310 | 10 519 950 |
| 96510070 | 15 300 | 11 979 900 |
| 96510080 | 14 400 | 14 976 000 |
| 96520300 | 8 155 | 7 298 725 |
| 96520400 | 13 250 | 16 761 250 |
| 96520500 | 13 255 | 10 894 790 |

We claim:

1. A process for preparing a human thrombin concentrate for therapeutic use comprising:
   (a) removing fibrinogen and prothrombin activation inhibitors from an initial PPSB fraction of human plasma by washing said fraction with sodium chloride;
   (b) activating prothrombin to produce thrombin in a solution by recalcifying said washed PPSB fraction by adding to the solution CaCl$_2$ at a concentration of 5 to 10 mM, subjecting the resulting mixture to an initial incubation period of about 2 hours at an initial incubation temperature of about 37° C. and subjecting this initially incubated mixture to a second incubation period of about 16 hours at about 24° C.;
   (c) purifying the activated, recalcified PPSB fraction by chromatographing on a strong cation exchange gel in the presence of sodium gluconate, to obtain purified human thrombin concentration.

2. The process according to claim 1, further comprising:
   (b1) subjecting said activated, recalcified PPSB fraction to viral inactivation by treating with a solvent-detergent, prior to said chromatographing.

3. The process according to claim 1, further comprising stabilizing said purified human thrombin concentrate by contacting said concentrate with a stabilizer mixture comprising albumin, saccharose, and calcium chloride.

4. The process according to claim 1, wherein said step (a) comprises washing said initial PPSB fraction with 0.2M to 0.23M sodium chloride in a citrate buffer solution in a column of DEAE-SEPHADEX and eluting said washing PPSB by increasing the sodium chloride concentration in said column to 0.5M.

5. The process according to claim 1, wherein said chromatographing is carried out on an agarose gel grafted with $CH_2-SO_3$ groups in a medium comprising 40 mM of sodium gluconate and 0.01M of sodium chloride at a pH of 6.5.

6. The process according to claim 1, wherein said step (c) further comprises eluting said purified human thrombin concentrate by increasing the eluant sodium chloride concentration to 0.2M and increasing the eluant sodium gluconate concentration to 150 mM.

7. The process according to claim 3, wherein said stabilizer mixture comprises 2 g/l of albumin, 5 g/l of saccharose, and 60 mM of $CaCl_2$.

8. The process according to claim 1, further comprising further concentrating said purified human thrombin concentrate, aliquoting said further concentrated purified human thrombin into aliquots having the volumes required for subsequent therapeutic use, and freeze-drying said aliquots.

* * * * *